United States Patent
Ludwig (10) Patent No.: US 9,492,413 B2
(45) Date of Patent: Nov. 15, 2016

(54) USE OF SALT OF AN ACETYLSALICYLIC ACID FOR THE TREATMENT OF VIRAL INFECTIONS

(75) Inventor: Stephan Ludwig, Munster (DE)

(73) Assignee: Ventaleon GMBH, Gauting (DE)

( * ) Notice: Subject to any disclaimer, the term of this patent is extended or adjusted under 35 U.S.C. 154(b) by 658 days.

(21) Appl. No.: 12/679,251

(22) PCT Filed: Jan. 14, 2009

(86) PCT No.: PCT/DE2009/000033
§ 371 (c)(1),
(2), (4) Date: Mar. 19, 2010

(87) PCT Pub. No.: WO2009/089822
PCT Pub. Date: Jul. 23, 2009

(65) Prior Publication Data
US 2012/0017892 A1    Jan. 26, 2012

(30) Foreign Application Priority Data
Jan. 14, 2008    (DE) .................. 10 2008 004 386

(51) Int. Cl.
| A61K 31/197 | (2006.01) |
| A61K 39/145 | (2006.01) |
| A61K 38/00  | (2006.01) |
| A61K 31/19  | (2006.01) |
| A61K 51/08  | (2006.01) |
| A61K 49/00  | (2006.01) |
| A61K 9/00   | (2006.01) |
| A61K 31/616 | (2006.01) |

(52) U.S. Cl.
CPC ............ *A61K 31/197* (2013.01); *A61K 9/008* (2013.01); *A61K 31/19* (2013.01); *A61K 31/616* (2013.01); *A61K 38/00* (2013.01); *A61K 39/145* (2013.01); *A61K 49/0004* (2013.01); *A61K 51/088* (2013.01)

(58) Field of Classification Search
None
See application file for complete search history.

(56) References Cited

U.S. PATENT DOCUMENTS

| 6,051,566 A      | 4/2000  | Bianco       |
| 2005/0171070 A1  | 8/2005  | Ecker et al. |
| 2006/0166901 A1  | 7/2006  | Yu et al.    |
| 2006/0247161 A1  | 11/2006 | Planz et al. |

FOREIGN PATENT DOCUMENTS

| CA | 2 473 893 A1   | 7/2003 |
| CN | 1642528        | 7/2005 |
| EP | 1 447 450 A1   | 8/2004 |
| GB | 2 306 109 A    | 4/1997 |
| JP | 48-56815       | 8/1973 |
| JP | 6-507404       | 8/1994 |
| JP | 2003-503320    | 1/2003 |
| JP | 2004-507463    | 3/2004 |
| JP | 2005-519892    | 7/2005 |
| JP | 2006-524640    | 11/2006 |
| WO | WO 02/05782 A2 | 1/2002 |
| WO | 02/098339 A2   | 12/2002 |
| WO | WO 2004/060360 A1 | 7/2004 |
| WO | WO 2006/128600 A2 | 5/2006 |
| WO | WO/2006/074114 | * 7/2006 |
| WO | 2006/097247 A1 | 9/2006 |
| WO | 2006/128600 A2 | 12/2006 |

OTHER PUBLICATIONS

Phillips et al., Inhaled lysine-aspirin as a bronchoprovocation procedure in aspirin-sensitive asthma: its repeatability, absence of a late-phase reaction, and the role of histamine, 1989, Journal of Allergy and Clinical Immunology, vol. 84, No. 2, pp. 232-241.*
Dewey, Homeopathy in Influenza-A chorus of Fifty in Harmony Clinical Medicine, 1921, Journal of the American Institute of Homeopathy, pp. 1038-1043.*
Centers for Disease Control and Prevention, CDC recommends that people with influenza-like illness remain at home until at least 24 hours after they are free of fever (100° F. [37.8° C.]), or signs of a fever without the use of fever-reducing medications., Oct. 23, 2009, Accessed at <<http://www.cdc.gov/h1n1flu/guidance/exclusion.htm>>, Sep. 20, 2010.*
Mazur et al., Acetylsalicylic acid (ASA) blocks influenza virus propagation via its NF-kB-inhibiting activity, 2007, Cellular Microbiology, vol. 9, No. 7, pp. 1683-1694.*
Translation of Office Action in corresponding Chinese Application No. 200980102181.8, dated Dec. 2, 2011, 10 pages.
Translation of Office Action in corresponding Japanese Application No. 2010-514691, dated Jun. 20, 2013, 3 pages.
L. Cappella et al., "Efficacy and tolerability of nimesulide and lysine-acetylsalicylate in the treatment of paediatric acute upper respiratory tract inflammation," Abstract, PubMED [Drugs. 1993], pp. 1.
Translation of Office Action in corresponding Israel Application No. 206450, dated Oct. 24, 2012, 2 pages.
Cappella, L., et al., "Efficacy and tolerability of nimesulide and lysine-acetylsallcylate in the treatment of paediatric acute upper respiratory tract inflammation," (Abstract), PubMed, Durgs, 46 Suppl. 1-222-5 (1993).
English language abstract of BE 1010692 (A6), Dec. 1, 1998.
English language abstract of CN 1418635 (A), May 21, 2003.
English language abstract of DE 100 34 802 (A1), Jan. 31, 2002.
English language abstract of DE 10 2005 053 358 (A1), May 10, 2007.
English language abstract of EA 000889 (B1), Jun. 26, 2000.
English language abstract of RU 2 131 750 C1,, Jun. 20, 1999.
Mazur, I. et al., "Acetylsalicylic Acid (ASA) Blocks Influenza Virus Propagation Via Its NF-κB-Inhibiting Activity," Cell. Microbiol., 9:1683-1694, (2007).
Dec. 22, 2015 Office Action for Japanese patent application No. 2010-541691.
English language abstract of JP 2005-519892.
English language abstract of WO 2006/128600.

* cited by examiner

*Primary Examiner* — Benjamin P Blumel
(74) *Attorney, Agent, or Firm* — Finnegan, Henderson, Farabow, Garrett & Dunner, L.L.P.

(57) ABSTRACT

The invention relates to a method of use of a composition comprising a salt of the o-acetylsalicylic acid with a basic amino acid for producing a pharmaceutical composition for the prophylaxis or treatment of viral infections of humans or of animals, in particular mammals and birds.

15 Claims, 13 Drawing Sheets

A/THAILAND/KAN-1/2004 (H5N1)
(8h p.i.)

UNTREATED CONTROL

SOLVENT

LG-ASA

NP          NP/DAPI

USE OF SALT OF AN ACETYLSALICYLIC ACID FOR THE TREATMENT OF VIRAL INFECTIONS

FIELD OF THE INVENTION

The invention relates to the novel use of a composition comprising a salt of o-acetylsalicylic acid with a basic amino acid for producing a pharmaceutical composition.

PRIOR ART AND BACKGROUND OF THE INVENTION

Influenza still belongs to the great plagues of mankind having a pandemic potential. There are only a few drugs against the inducing pathogens, the influenza A viruses, which are all immediately directed against the virus. The problem is that resistances can develop relatively quickly. Further, there is a risk that the avian influenza epidemically growing in fowl, induced by infections with the H5 influenza A virus, is also transmissible to humans. In particular persons that come into contact with infected fowl are therefore at high risk. In particular it has to be noted that increasingly insensitivities of the H5N1 viruses against the few approved drugs such as oseltamivir are reported. There is therefore an urgent need of novel and efficient anti-influenza drugs for the prophylaxis as well as for the treatment of viral infections, and the drugs should not trigger any resistances if possible.

From the document WO2004/060360 A1, it is known that acetylsalicylic acid is able to inhibit the transcription factor NF-κB in host cells and that in the course of this inhibition of the NF-κβ signal pathway essential viral components will remain in the cell nucleus and cannot be integrated anymore in viral particles. From this document is further known the aerogenic administration of acetylsalicylic acid for the prophylaxis or treatment of viral infections.

For instance, from the document DE 102 02 019 A1, salts of the acetylsalicylic acid with basic amino acids are known in the art, the preparations obtained therewith being provided exclusively for the oral administration. From this document, further, the use of such salts for treating diseases of the rheumatic type, arthritides, neuralgias, myalgias, migraine, ischemic heart diseases, stroke, angina pectoris, myocardial infarct, bypass operations, PTCA, stent implantations, for the stimulation of the immune system of HIV patients, for the tumor prophylaxis, for the retardation of the cognitive decline due to the dementia syndrome, for the inhibition of gallstone formation and/or the treatment of diabetic diseases is known. The insofar known salts are furthermore already used under the trade name Aspisol® as drugs for treating asthma, hay fever, swellings of the nasal mucosa or chronic respiratory tract infections, and that in addition to the oral administration also for the injection. All these diseases do not have a direct correlation to viral infections by influenza viruses.

The use of pure acetylsalicylic acid as an antiviral agent, which is inhalatively administered as an aerosol into the respiratory tract or the lung, has proven itself in principle very well in the animal model. For humans, inhalation of pure acetylsalicylic acid may however cause strong irritations of the respiratory tract. Further, in individual cases, it was shown that an inhalation of acetylsalicylic acid may lead to asthma attacks for some sensitive patients. In any case, an aerogenic application of acetylsalicylic acid as an anti-influenza drug would therefore be contraindicated for asthma patients or persons with an asthma risk.

TECHNICAL OBJECT OF THE INVENTION

It is therefore the object of the invention to provide a formulation with acetylsalicylic acid for treating viral infections, which is particularly well tolerated and in particular reliably avoids the risk of the induction of asthma attacks.

Basics of the invention and preferred embodiments.

DETAILED DESCRIPTION

For achieving this technical object the invention teaches the use of a composition comprising a physiologically effective dose of a salt of the o-acetylsalicylic acid with a natural or non-natural basic amino acid for producing a pharmaceutical composition for the prophylaxis or treatment of viral infections of humans or of animals, in particular of mammals and birds. For the purpose of the invention, in particular infections with naturally occurring wild-type viruses, not however infections with genetically modified viruses are designated viral infections.

Among the birds, in particular fowl, such as hens, gooses, ducks, poulards, turkeys, quails, or doves, but also songbirds are involved for the prophylaxis or treatment.

By the use of such a salt, in particular with aerogenic administration, an irritation of tissue, for instance of the mucosae of the respiratory tract, is avoided by that the active substance in the administered formulation is not acid. Thereby, in particular asthma attacks in patients affected with asthma or persons at risk are reliably prevented, and there are practically no obstacles for a broad application as a therapeutic agent as well as a prophylactic agent because of the freedom from side effect risks, the more since the formulation is even already used as an agent against asthma. Furthermore, as has been found by the invention, the inhibition of the viral replication is practically not affected by the derivatization of the acetylsalicylic acid, what could not be expected; surprisingly it is even in part slightly increased.

It is preferred, if the basic amino acid is selected from the group consisting of lysine, arginine, ornithine, diaminobutyric acid, and mixtures of such acids, preferably it is a mono-acetylsalicylate. An amino acid is an alpha-aminocarboxylic acid, and at the alpha-atom, a hydrogen or an arbitrary radical can be bound as a side chain. A basic amino acid comprises in the side chain a basic group or several basic groups, in particular an amino group. The basic amino acid may in particular be D-lysine, L-lysine or a mixture of D-lysine and L-lysine.

The preparation may in addition comprise a salt of the o-acetylsalicylic acid with a natural or non-natural amino acid with a non-basic side chain, in particular with glycine. The weight ratio lysine to glycine in the composition may be in the range from 100:1 to 1:1, in particular 100:1 to 10:1. Preferred is a mixture of salts of the amino acids lysine and glycine. Particularly preferred is a salt or a mixture of salts, such as the composition commercially available under the trade name Aspisol®, for instance in an aqueous solution.

For the purpose of the invention, pharmaceutical compositions may also be used, which contain prodrugs, which are naturally metabolized into active substances used according to the invention by the organism after taking or administration.

According to the invention, the used composition can be used for the prophylaxis or treatment of a multitude of viral infections. Particularly suitable is the composition for the prophylaxis or treatment of infections with negative-strand RNA viruses, such as influenza viruses, preferably influenza A viruses, in particular viruses of the H5 or H7 type.

It has however also been found that the substance used according to the invention suppresses the over-expression of virus-induced cytokines ("cytokine storm"), which are regulated in a NF-κB-dependent manner. By means of the substance according to the invention, therefore, the pathogenity of many viruses can generally be reduced, the pathogenic potential of which is correlated, among others, with an excessive cytokine expression. Therefore, the composition used according to the invention is also suitable for the treatment and prophylaxis of viral infections with coronavirus (SARS), respiratory syncytial virus (RSV), filoviruses, such as Marburg virus or Ebola virus, arena viruses, such as Lassa virus, Argentinean, Bolivian or Venezuelan hemorrhagic fever viruses, hantaviruses, flaviviruses, such as Dengue virus or yellow fever virus, Crimean-Congo hemorrhagic fever virus, Rift Valley fever virus, parainfluenza viruses (type 1, 2 and 3), rhinoviruses, human metapneumoviruses (hMPV) and Epstein Barr virus.

The galenic preparation of a pharmaceutical composition used according to the invention can be made in a way being usual in this technology and can in principle take place in an arbitrary type of administration, for instance orally, for the injection or aerogenically for the inhalation. Suitable solid or liquid galenic preparation forms are for instance granulates, powders, dragees, tablets, (micro) capsules, suppositories, syrups, juices, suspensions, emulsions, drops or injectable solutions (i.v., i.p., i.m., s.c.) or fine dispersions (aerosols), transdermal systems, and preparations with protracted release of active substance, for the production of which usual means are used, such as carrier substances, explosives, binding, coating, swelling, sliding or lubricating agents, tasting agents, sweeteners and solution mediators. As auxiliary substances are named here magnesium carbonate, titanium dioxide, lactose, mannite and other saccharides, talcum, milk protein, gelatin, starch, cellulose and their derivatives, animal and vegetable oils such as codliver oil, sunflower oil, peanut oil or sesame oil, polyethylene glycols and solvents, such as sterile water and mono or multi-valent alcohols, for instance glycerine, or mixtures of such solvents. A pharmaceutical composition according to the invention can be produced by that at least one salt used according to the invention is mixed in a defined dose with a pharmaceutically suitable and physiologically well tolerated carrier and possibly further suitable active, additional or auxiliary substances, and is prepared in the desired form of administration. Examples of preparations for the oral administration are for instance found in the document DE 102 02 019 A1 and the documents cited therein.

Preferred is, however, the galenic preparation for the aerogenic, nasal administration as a liquid, aqueous composition (solution), or as a powder, if applicable in a suspension in a propellant, for instance a propellant to be liquefied at room temperature, such CFCs, hydrofluoroalkanes, such as 1,1,1,2-tetrafluoroethane or 1,1,1,2,3,3,3-heptafluoropropane, propane, butane, isobutane, or other propellants being usual in the field of the medical aerosol formulations. In addition to the mentioned propellants or in their place, air, oxygen, nitrogen, carbon dioxide or nitrous oxide can also be used. The composition may comprise the usual additional and auxiliary substances of the medical aerosol formulations, such as for instance physiologically well tolerated surface-active substances, and/or conventional dispersing agents.

The aqueous composition further preferably is a 0.01 mM to 3.0 M, preferably 0.5 to 3.0 M, or 0.01 to 100 mM, in particular 0.1 to 10 mM, aqueous solution of the salt or of the mixture of salts.

It is preferred, if the particle size of the aerosols, be it the solution, be it the salt as a solid material or a suspension, has an MMAD value (mass median aerodynamic diameter) smaller than 10 µm, preferably smaller than 5 µm. For the measurement of the aerodynamic particle size distribution FPD (fine particle dose) or FPF (fine particle fraction), impactors are suitable, such as for instance the 5-stage Multistage Liquid Impinger (MSLI) or the 8-stage Andersen Cascade Impactor (ACI), which are described in chapter 601 of the United States Pharmacopoeia (USP) or in the Inhalanda Monograph of the European Pharmacopoeia (Ph. Eur.). Based on the aerodynamic particle distribution, the MMAD value of an aerosol preparation can be calculated by means of a "log-probability plot". By the preferred MMAD values, it is achieved that the aerosol particles are respirable, and that down to the deep part of the lung, so that a sufficient concentration in the whole lung is obtained for the usual durations of the administration. In order to prevent that small particles are exhaled again, a lower limit for the MMAD value of 0.1 µm, preferably 0.5 µm, most preferably 1 µm can be provided.

The salt used according to the invention may be reduced to small pieces or micronized in a conventional manner for obtaining the desired MMAD values, for instance by means of pinned disk, ball or air separation mills.

The administration of an aerosol according to the invention can be made with all inhalation devices with aerosol generators, such as vaporizers or nebulizers, as they are usual in the medical field. Examples are powder-aerosol vaporizers or DPI (dry powder inhalators), nozzle, ultrasound, or oscillating membrane nebulizers. Further can be used aerosol generators, which utilize the elektrohydrodynamic principle, or condensation aerosols from a liquid formulation. Examples for suitable inhalation devices are described in the documents EP 1741460 A, EP 1700614 A, EP 1258264 A and EP 1163921 A.

The concentration of the salt in the composition in connection with the throughput rate of an employed aerosol generator is selected such that at least 10 mg, preferably at least 50 mg, most preferably at least 100 mg, of the salt are transformed into the aerosol and administered to a patient within a time of less than 5 min, preferably 2 min, most preferably 1 min.

Furthermore, it is useful for an optimum lung deposition, if the inspiratory flow or the inspiratory volume is checked and adjusted. With a too fast inhalation flow, the aerosol particles will already hit against the pharyngeal background or are separated at the glottis. If the breathing is too flat, the aerosol particles will only reach the upper respiratory tract and not the deep parts of the lung. An employed inhalation system should therefore guarantee a deep, slow inhalation by a patient. For children, the inhalation volume should be at least 200 ml, preferably at least 500 ml. For adults, the inhalation volume should be at least 300 ml, preferably at least 500 ml. Suitably, an inhalation of such an aerosol volume takes place over a time of at least 1 s, better at least 3 s, preferably at least 5 s. The inhalation flow is advantageously adjusted to less than 1,000 ml/s, in particular less than 500 ml/s, in particular less than 300 ml/s, and the breathing volume to at least 20%, in particular at least 30%, preferably at least 50%, up to 95%, referred to the inspiration capacity of a patient. The latter secures on the one hand a slow, however on the other hand also a deep inhalation by a patient.

For the purpose of the invention, inhalation systems can be used, which measure the above parameters by means of sensors and provide information about the proper or not proper inhalation by means of electrical, acoustic and/or optical signals. With regard to inhalation devices working in this way, reference is made to the above documents. In the case of simple inhalation systems, it may also be provided that a patient information sheet with the mentioned measures is added to the pharmaceutical composition.

Therefore, the invention also relates to an aerosol formulation comprising a salt of the o-acetylsalicylic acid with a natural or non-natural basic amino acid, a propellant and optionally auxiliary and/or carrier substances. The salt may be comprised in an amount of 0.01 to 50 wt-%, 0.001 to 10 wt-%, in particular 0.1 to 10 wt-%, or 10 to 50 wt-%, in 0.02 particular 30 to 50 wt-%, referred to the complete formulation. If the salt exists in 0.03 particle form, it may be comprised with an MMAD value of less than 10 μm, in 0.04 particular less than 5 μm.

It is surprising, in particular when using the above high concentrations that aerosol particles, which are generated from such solutions, can be produced with the above mentioned small particle size.

Further, the invention also relates to the use of an aerosol formulation according to the invention for the prophylaxis or treatment of viral infections of humans or of animals, wherein a human, who is at risk to catch a viral infection or is affected therewith, or such an animal is administered aerogenically for the inhalation through the nose or the mouth a physiologically effective amount of the aerosol formulation.

Finally, the invention relates to an inhalation device with a supply tank and an aerosol generator connected to the supply tank, wherein the supply tank comprises an aerosol formulation according to the invention. To the output of the aerosol generator is usually connected a mouthpiece. Further, an air pump may be provided, by means of which under control by a control device the inhalation flow and/or the inhalation volume are controlled. Control and/or regulation means for the control and/or regulation of the inhalation flow and of the breathing volume may be provided, and the control and/or regulation means are preferably adjusted to the above values.

The above explanations for the pharmaceutical composition according to the invention apply in an analogous manner also to the aerosol formulation according to the invention, to the use thereof and to the inhalation device.

In the following, the invention is explained in more detail with reference to examples.

Example 1

Investigation of Resistance Phenomena

Since particularly the resistance problems with acetylsalicylic acid as a antivirally acting inhibitor of cellular factors should be addressed, the tendency for the formation of resistant variants was compared to the drugs amantadine and oseltamivir directly acting on the virus. A549 lung epithelial cells were infected with the highly pathogenic avian influenza A virus isolate A/FPV/Bratislava/79 (H7N7) (FPV, fowl plague virus) with an MOI=0.01 (multiplicity of infection) and incubated for another 24 h in presence or absence of acetylsalicylic acid (5 mM), amantadine (5 μM) and oseltamivir (2 μM). In a separate batch, A549 lung epithelial cells were infected with A/FPV/Bratislava/79 (H7N7) with an MOI=0.001 and incubated for another 24 h in presence or absence of lysine-glycine-acetylsalicylate (5 mM) and oseltamivir (2 μM). For both batches then the cell supernatant of each sample was collected, and the viral titer in the plaque assay on MDCK cells was determined. The supernatants were then normalized and again used to infect with respectively identical numbers of viruses a second treated or untreated cell passage under the same conditions. This procedure was repeated in total up to the fifth or eighth passage.

Figure 1A:
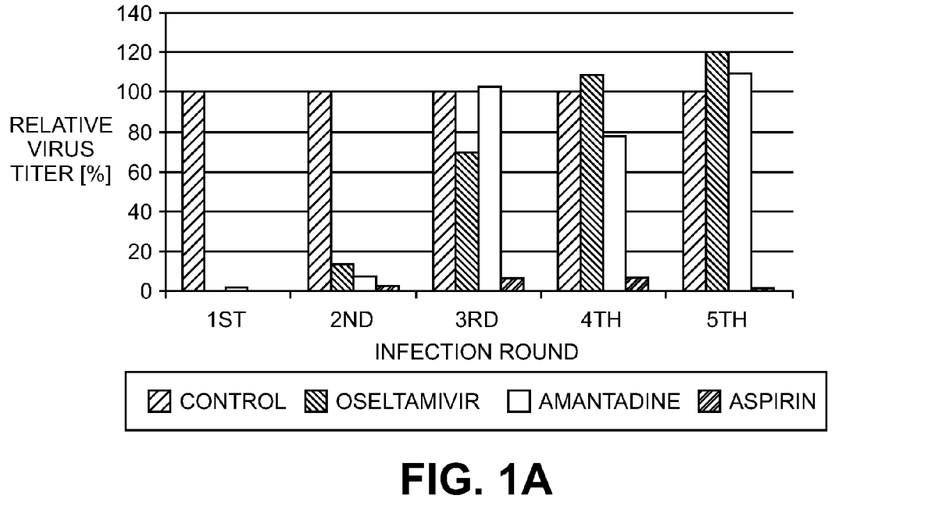
FIGS. 1A and 1B show that acetylsalicylic acid as well as lysine-glycine-acetylsalicylate have no tendency at all for the formation of resistant variants in cell culture.
Figure 1B:
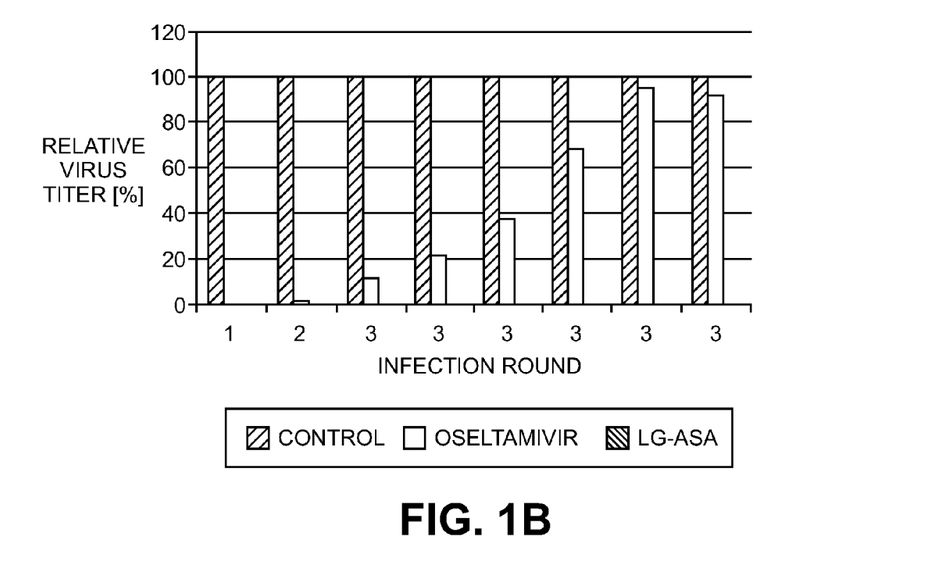

In FIG. 1A the virus titers of cells treated with acetylsalicylic acid or amantadine or oseltamivir were compared to the titers of the supernatants of untreated cells. It can be seen in the third passage already that the virus titers of amantadine-treated cells are again significantly increased because of the formation of resistant variants. Surprisingly this is also found to a comparable extent under the experimental conditions chosen here for oseltamivir. In a clear contrast thereto, it is found that acetylsalicylic acid has even in the fifth passage still the unchanged same antiviral activity as in the first passage. In FIG. 1B the virus titers of cells treated with lysine-glycine-acetylsalicylate or oseltamivir were compared to the titers of the supernatants of untreated cells. The result described in FIG. 1A is also obtained for lysine-glycine-acetylsalicylate, and even after eight passages there is still no viral resistance formation after lysine-glycine-acetylsalicylate treatment detectable. The obtained results are suitable to full extent to state that acetylsalicylic acid as well as lysine-glycine-acetylsalicylate have no tendency at all for the formation of resistant variants in cell culture.

Example 2

Investigation of the Formulation Lysine-Glycine-Acetylsalicylate for Antiviral Activity Against Highly Pathogenic Influenza A Viruses The investigated composition is lys-gly-acetylsalicylate (in the following also called LG-acetylsalicylate), which corresponds to the molecular composition of the product Aspisol®, available from Bayer AG.

Figure 2:
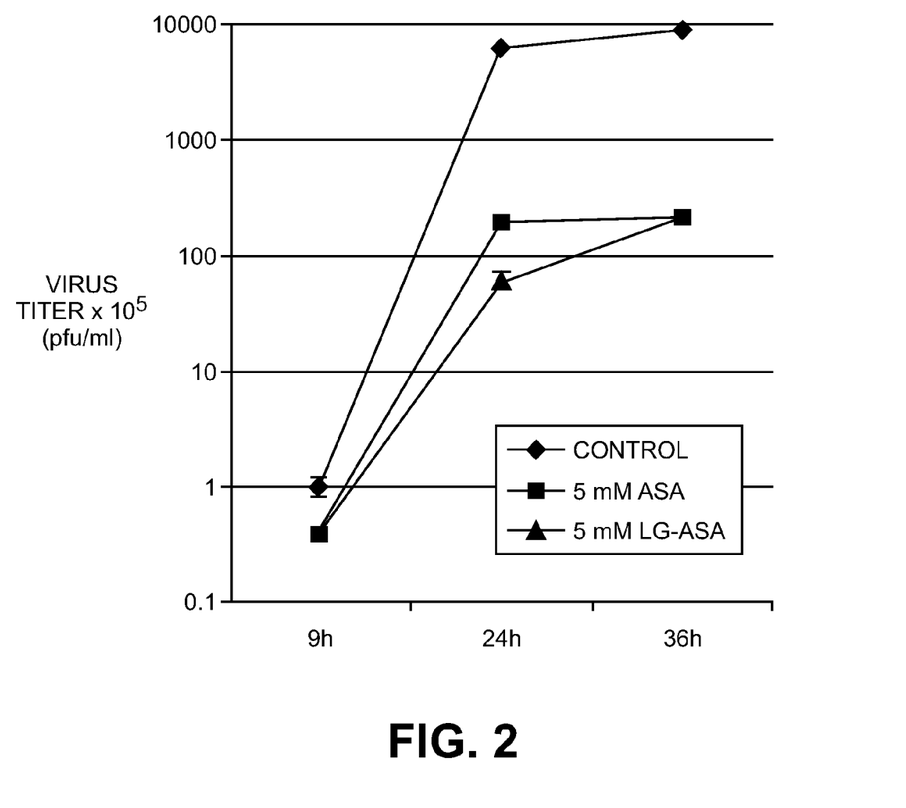
FIG. 2 shows a plot of the virus titers versus time. The result is that LG-acetylsalicylate equally efficiently inhibits the virus multiplication of the highly pathogenic avian H7N7 isolate as acetylsalicylic acid.

This formulation was subjected to the investigations for antiviral activity against influenza viruses. A549 lung epithelial cells were infected with A/FPV/Bratislava/79 (H7N7) (MOI=0.01) and incubated for 8 h, 24 h and 36 h in presence or absence of acetylsalicylic acid (5 mM) or LG-acetylsalicylate (5 mM). The cell supernatant of each sample was then collected, and the viral titer in the plaque assay on MDCK cells was determined therefrom. FIG. 2 shows a plot of the virus titers versus time. The result is that LG-acetylsalicylate equally efficiently inhibits the virus multiplication of the highly pathogenic avian H7N7 isolate as acetylsalicylic acid.

Figure 3A:
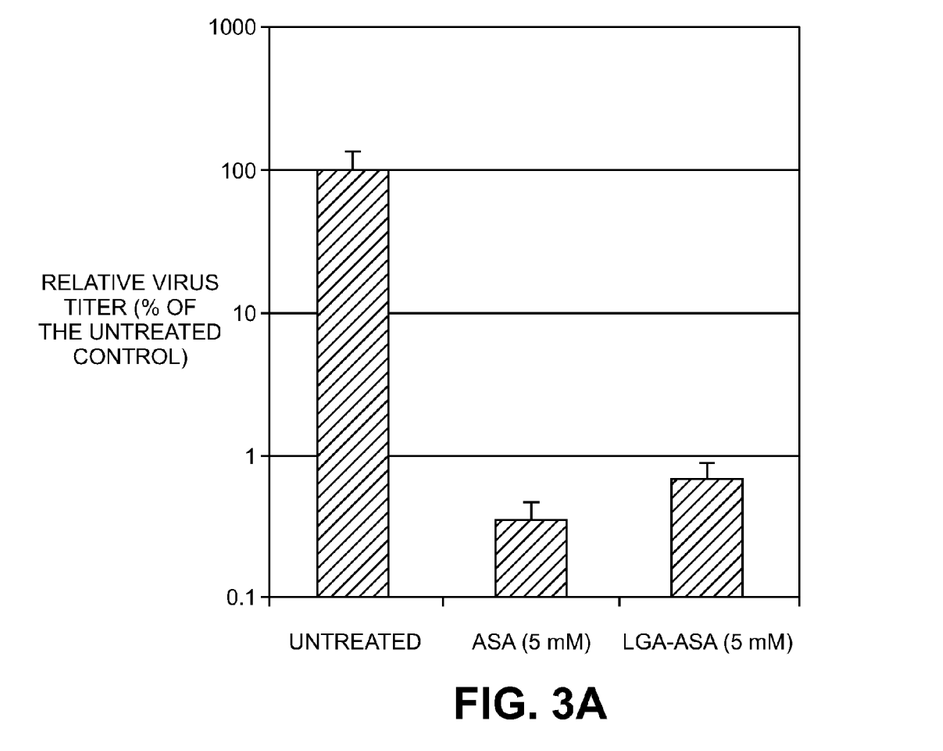
FIGS. 3A and 3B show an efficient inhibition of the virus titers of the H5N1 strain by several decimal powers.
Figure 3B:
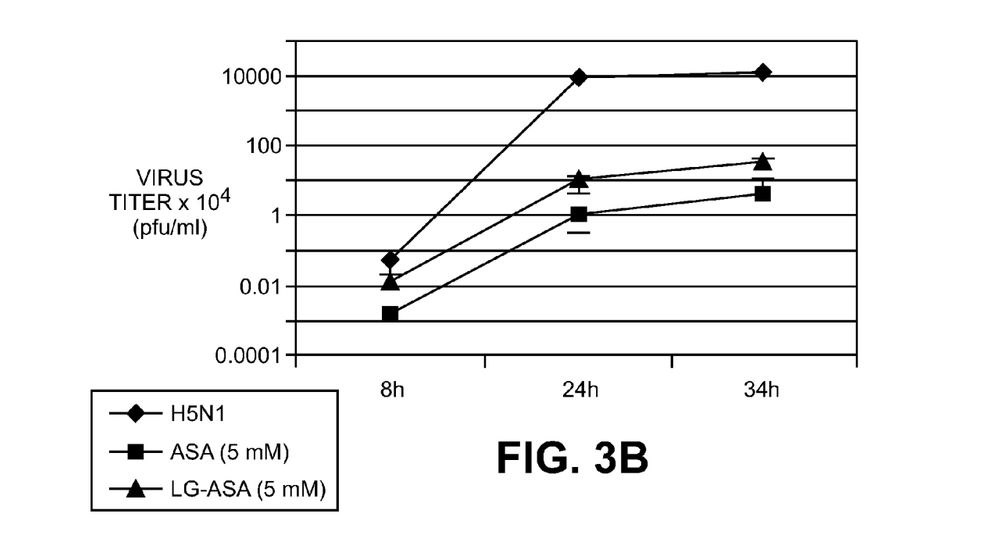

This is, as shown in FIG. 3, also the case after infection with highly pathogenic isolates of the subtype H5N1. A549 lung epithelial cells were infected with the human H5N1 isolate A/Thailand/KAN-1/2004 (MOI=0.001) and incubated in presence or absence of acetylsalicylic acid or LG acetylsalicylic acid in the mentioned concentrations. The cell supernatant was investigated for the determination of the virus titers in the plaque assay on MDCK cells. FIG. 3A shows a time value of 20 h, in FIG. 3B the virus titers are shown in a growth kinetics diagram. In both cases, an efficient inhibition of the virus titers of the H5N1 strain by several decimal powers can be seen.

Because of the high antiviral potential in vitro, it can be assumed that the formulation LG-acetylsalicylate is suitable as an anti-influenza active substance for an inhalative administration.

Example 3

Influence of LG-Acetylsalicylate on Highly Pathogenic Avian Influenza Viruses in the Cell Culture System MDCKII cells were cultivated in MEM medium (MEM; Gibco (Invitrogen) Germany 21430-079, lot 32034) with the addition of 10% heat-deactivated fetal calf serum (FCS, PAA Laboratories/A04305-0346), penicillin (Grünenthal/616G03) and streptomycin (Sanavita/03056440111). For the infection the cells were sown in 24-well plates (8×104 cells/well; Greiner, Germany, No. 662160, lot 05210151) and incubated over night at 37° C. Before the infection, the cells were washed with PBS, the corresponding virus (FPV, SN1, MB1) was diluted in PBS/BA (PBS supplemented with 0.6% BA (MP Biomedicals), 1 mM MgCl2, 0.9 mM CaCl2, penicillin (Grünenthal/616G03) and streptomycin and pipetted with an MOI of 0.001 on the cell lawn. After an incubation time of 30 min at 37° C., the virus inoculum was removed, to the cells was added either 1 ml MEM medium or MEM medium, which contained 5 mM LG-acetylsalicylate. After 8, 24, 32 and 48 hours after the infection, the respective supernatant was taken out. The presence of infectious virus particles was verified in a "plaque assay".

For the "plaque assay", MDCKII cells were sown in 96-well plates such that the cell lawn was confluent on the next day. The cells were washed with PBS and infected with dilutions of the supernatants, which were laid out in PBS/BA, for 60 min at 37° C. After the incubation, the cells were coated with an Avicel medium mixture (Avicel RC-581 (FMC/B624C)). For this purpose, a 2.5% Avicel solution was mixed with the same amount 2× MEM medium. After an incubation time of 20 h, the Avicel medium mixture was removed, the cells were fixed with a 4% Roti®-Histofix (Roth/32789170) solution in PBS for 30 min at 4° C. and then washed with PBS. The following work steps being necessary for the staining were carried out at room temperature. By the incubation with 0.3% Triton-X-100 (Serva/30043) in PBS, the cells were permeabilized. Virus-infected cells were stained by an immunohistological method. For this purpose, the cells were incubated for 1 h with a monoclonal antibody (Serotec/250107), which is specific for the influenza A virus nucleoprotein. The detection of the infected cells took place by another incubation (30 min) with a peroxidase-coupled anti-mouse antibody (DIANOVA/75790) and the addition of the True Blue™ peroxidase substrate (KPL/070490). The antibody dilutions were carried out in PBS with 10% FCS and 0.1% Tween-20 (Serva/16211). After the incubation with the primary and secondary antibody, the cells were washed three times for 5 minutes with PBS/0.1% Tween-20. For stopping the reaction, the plates were washed with tap water and dried. Dries plates were scanned and evaluated by means of the Corel DRAW 9.0 software. In order to determine the virus titer of the supernatants, the accumulations of infected cells (foci) in each well of the 96-well plate were counted. The number of counted foci was multiplied with the respective dilution factor. From the calculated values, the mean value was determined for each sample. The virus titer was recorded as log 10 of the mean values.

Figure 4A:
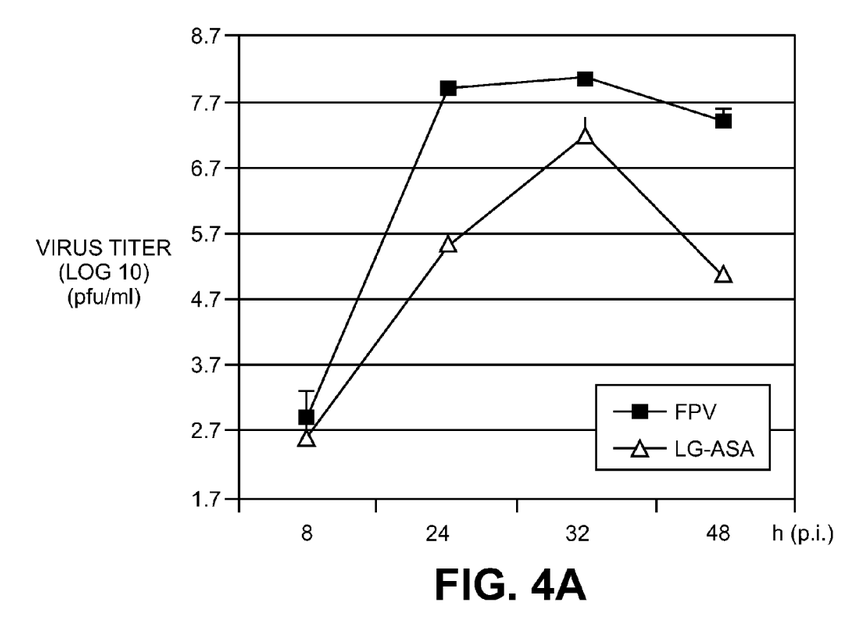
FIGS. 4A and 4B show a replication of an H7N1 virus (FPV) as well as of an H5N1 virus (MB1) by treatment with LG-acetylsalicylate is reduced in the cell culture system in part by more than 99%.
Figure 4B:
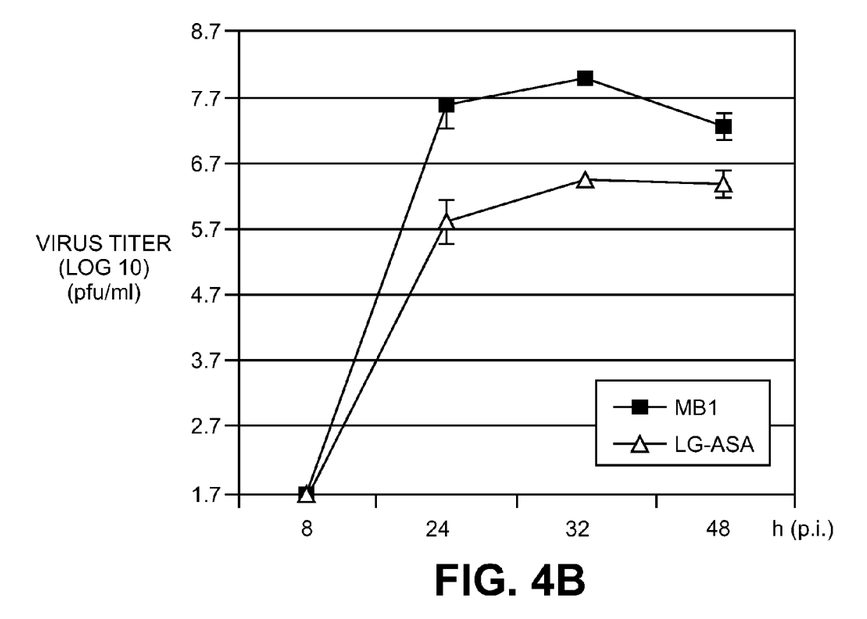

The results are shown in FIG. 4. It can be seen that the replication of an H7N1 virus (FPV) as well as of an H5N1 virus (MB1) by treatment with LG-acetylsalicylate is reduced in the cell culture system in part by more than 99%.

Example 4

Figure 5:
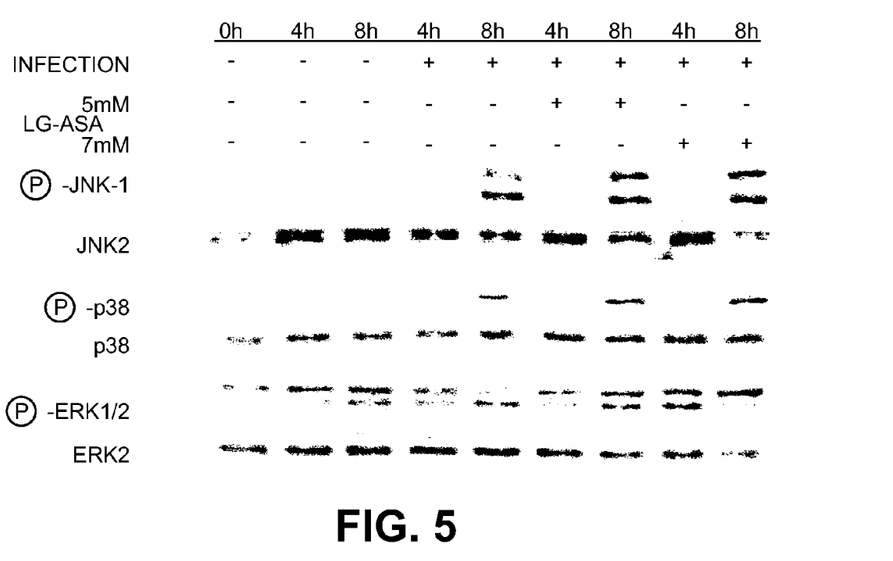
FIG. 5 shows the virus-induced activation of JNK, p38 and ERK (FIG. 5, track 5), which can be detected by means of phosphor-specific antibodies against the active form of these kinases in the Western blot, is not blocked by addition of 5 mM (track 7) or 7 mM acetylsalicylic acid (track 9).
Figure 6:
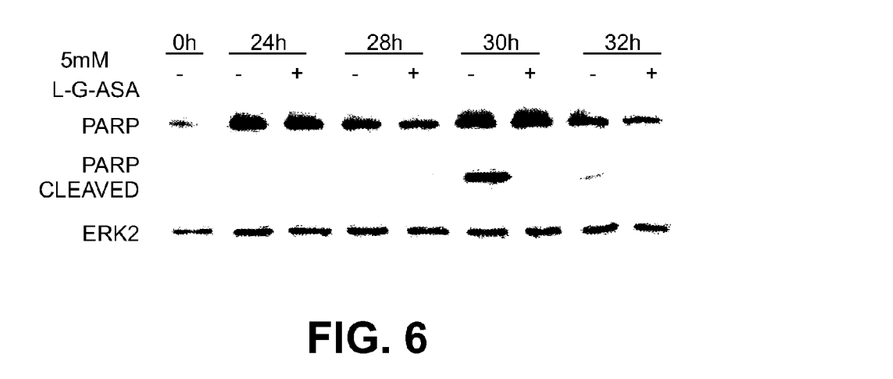
FIG. 6 shows the band of the cleaved PARP (track 6) being clearly visible after 30 h is efficiently reduced in LG-acetylsalicylate-treated samples (track 7).

Investigation of the Molecular Mechanisms of Action the Antiviral Activity of LG-Acetylsalicylate is Based on Further, it was investigated whether the molecular profile of action of LG-acetylsalicylate is comparable with that of the pure substance acetylsalicylic acid. LG-acetylsalicylate should act as an NF-κB inhibitor and correspondingly not have any side effects on other virus-induced signal pathways. An important group of signal mediators, which are also activated after influenza virus infection, are the so-called mitogen-activated protein kinases (MAPK). Thereto belong the kinases JNK, p38 and ERK. For the pure substance acetylsalicylic acid, it has already been shown that the virus-induced activation of these kinases is not inhibited by acetylsalicylic acid. As FIG. 5 shows, this is also the case for LG-acetylsalicylate: the virus-induced activation of JNK, p38 and ERK (FIG. 5, track 5), which can be detected by means of phosphor-specific antibodies against the active form of these kinases in the Western blot, is not blocked by addition of 5 mM (track 7) or 7 mM acetylsalicylic acid (track 9). Acetylsalicylic acid acts in an antiviral manner by the inhibition of the expression of proapoptotic factors, which finally will lead to a reduced caspase activation in the cell. FIG. 6 shows this also for LG-acetylsalicylate based on a Western blot, the caspase activation by the cleavage of the caspase substrate poly-ADP-ribose polymerase (PARP). The band of the cleaved PARP (track 6) being clearly visible after 30 h is efficiently reduced in LG-acetylsalicylate-treated samples (track 7).

Figure 7:
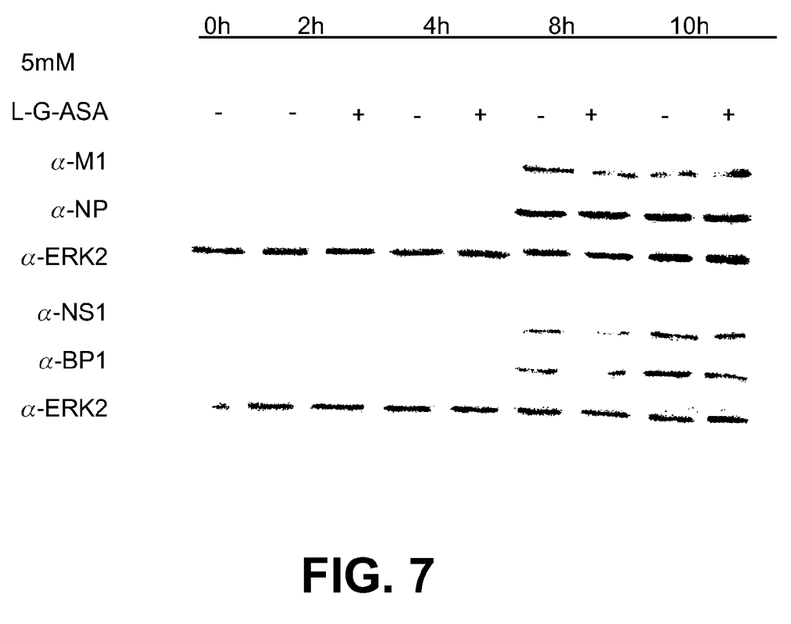
FIG. 7 shows in a Western blot that the accumulation of the viral proteins M1, NP, NS1 and PB1 is not inhibited by LG-acetyl-salicylate.
Figure 8:
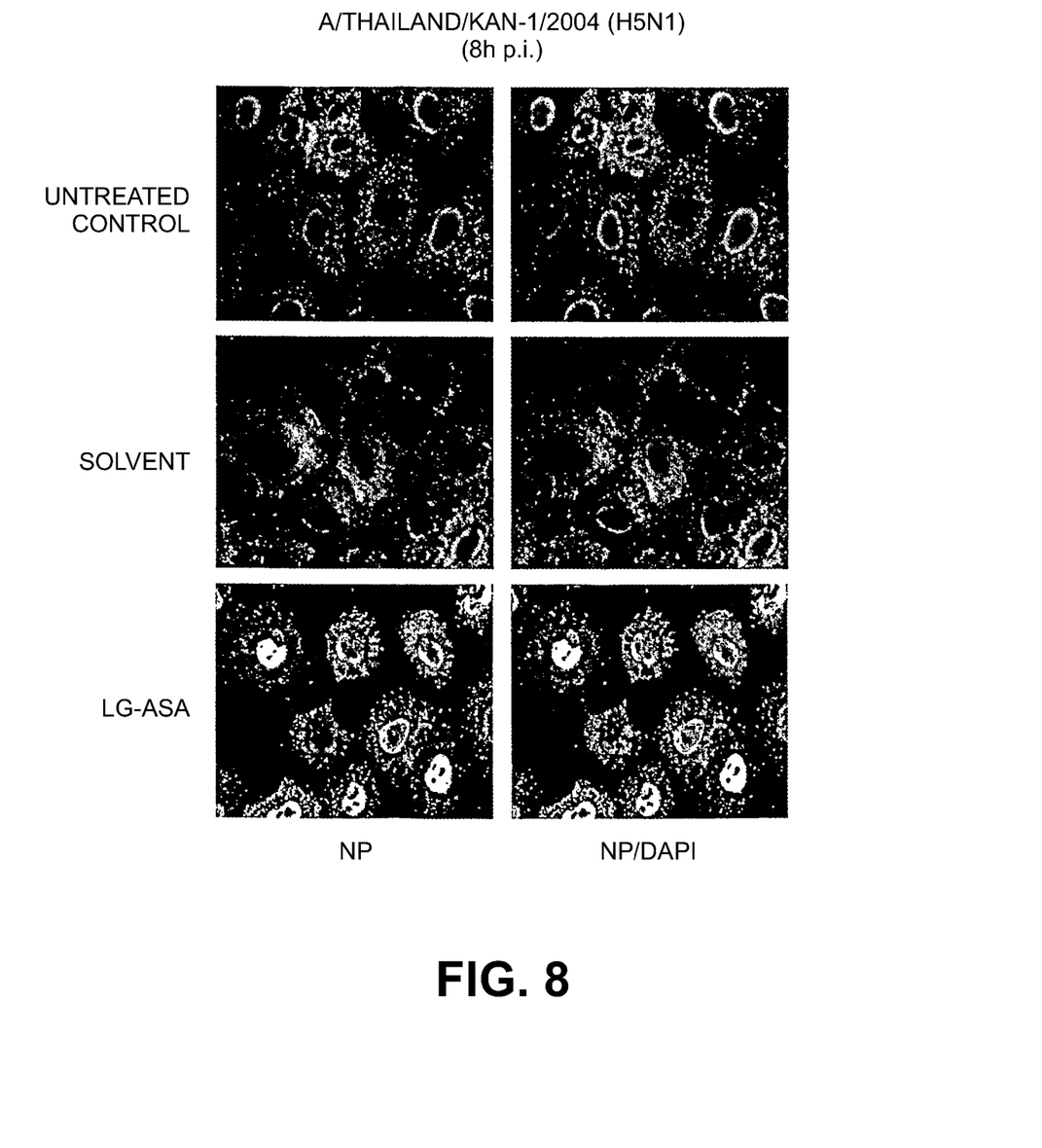
FIG. 8 shows an efficient retention of viral RNP complexes

The NF-κB-dependent step in the virus replication is the caspase-dependent export of viral ribonucleoprotein complexes (RNP) into the cytoplasm, which can then be built in at the cell membrane in new virus particles. Acetylsalicylic acid specifically blocks this step, without acting on the accumulation of viral proteins in an earlier stage of the multiplication cycle. For LG-acetylsalicylate the identical mechanism of action applies: FIG. 7 shows in a Western blot that the accumulation of the viral proteins M1, NP, NS1 and PB1 is not inhibited by LG-acetyl-salicylate. It is however found, same as described before for the pure substance acetyl-salicylic acid, an efficient retention of viral RNP complexes, as will become clear from the immunofluorescence analyses shown in FIG. 8.

Therefrom, the conclusion can be drawn that LG-acetylsalicylic acid has the same antiviral potential as acetylsalicylic acid and acts by identical molecular mechanisms in an inhibiting manner on the virus multiplication.

Example 5

Reduction of the IP10 and Interferon-Gamma m-RNA Expression Level after LG-Acetylsalicylate Treatment It is known that an excessive cytokine production, the so-called cytokine storm, is an important pathogenity factor for infections by H5N1 influenza viruses. Since most of these cytokines are regulated in an NF-κB-dependent manner, it was verified whether LG-ASA can inhibit the expression of virus-induced cytokines and can thus in addition influence indirectly the pathogenity of these viruses. From own preparatory work, it was known that IP10 and IFN-gamma is regulated up after infection with H5N1 (MB1) in mouse lungs. The expression of this chemokine or cytokine is induced by the transcription factor NF-κB. Based on earlier findings, it could be shown that Aspirin acts as an NF-κB inhibitor.

Figure 9:
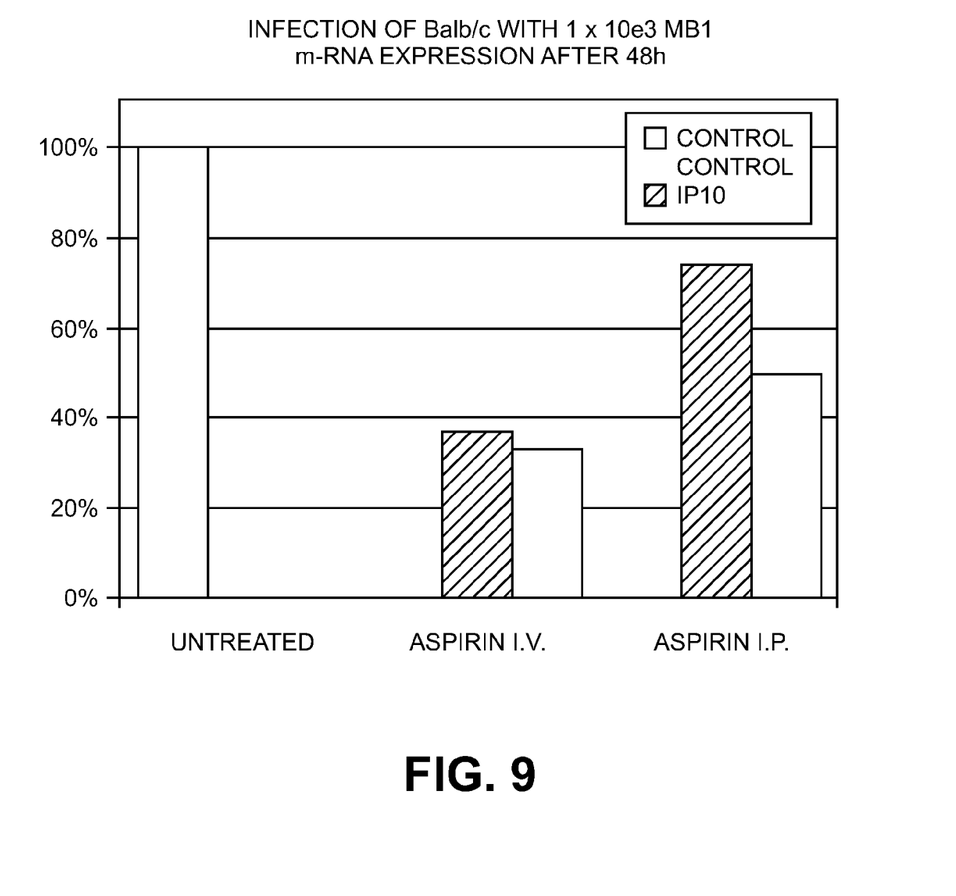
FIG. 9 shows the expression of IP10 and IFN-gamma in the mouse lungs of LG-acetylsalicylate-treated mice compared to the control animals.
Figure 10A:
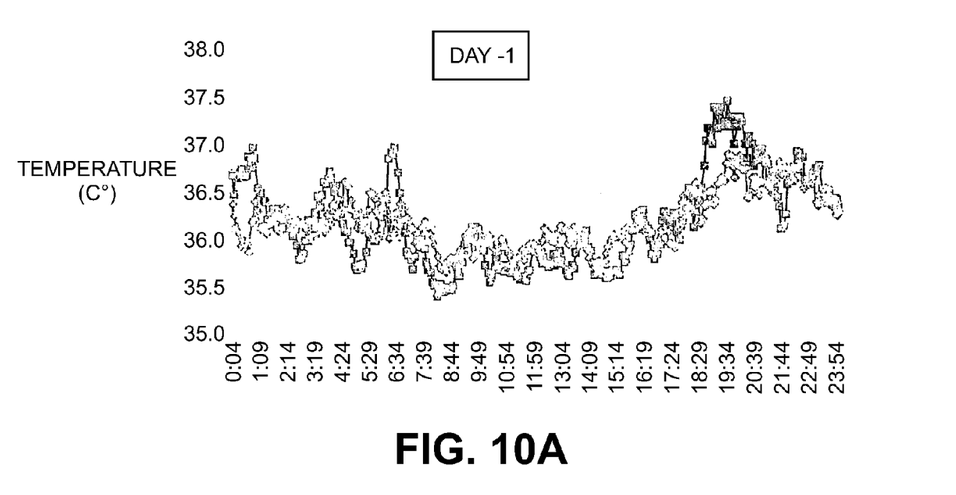
FIGS. 10A-10F show the compatibility of LG-acetylsalicylate after aerosol treatment of mice where the temperature was measured in increments of 5 minutes.
Figure 10B:
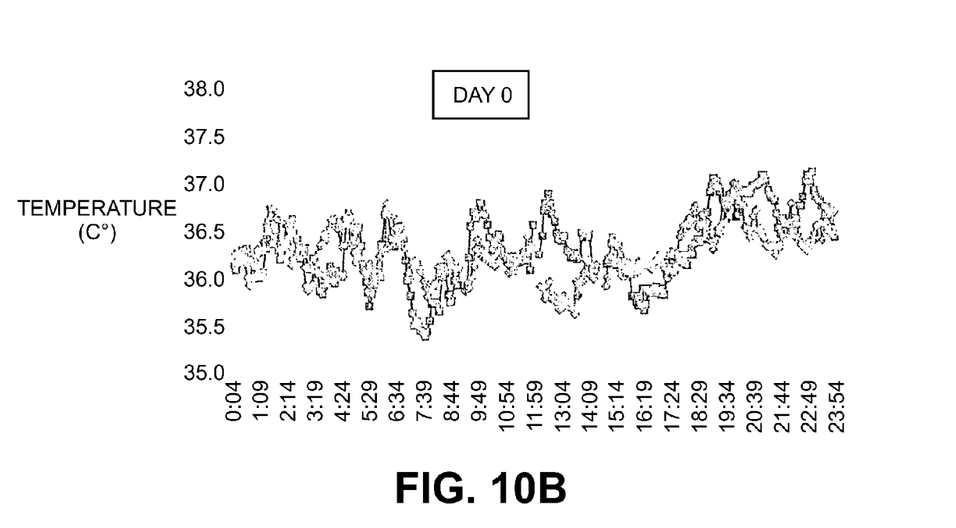
Figure 10C:
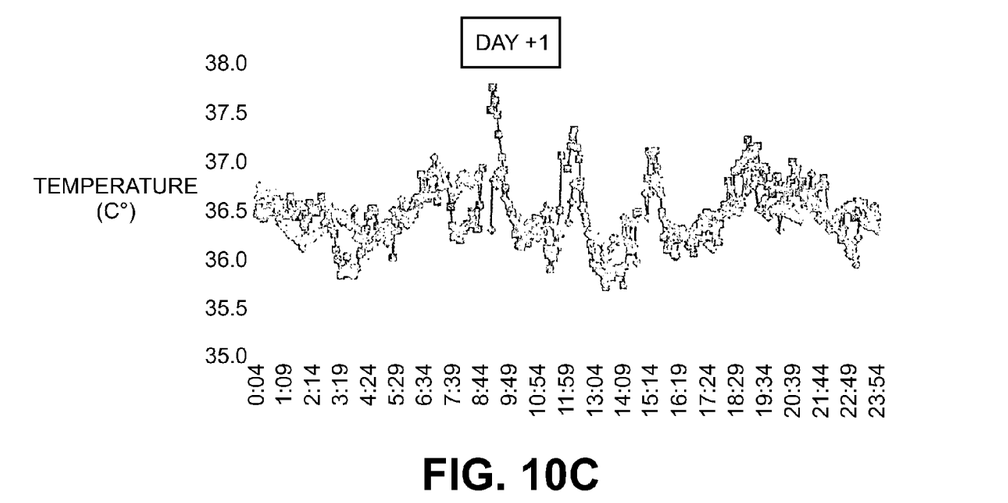
Figure 10D:
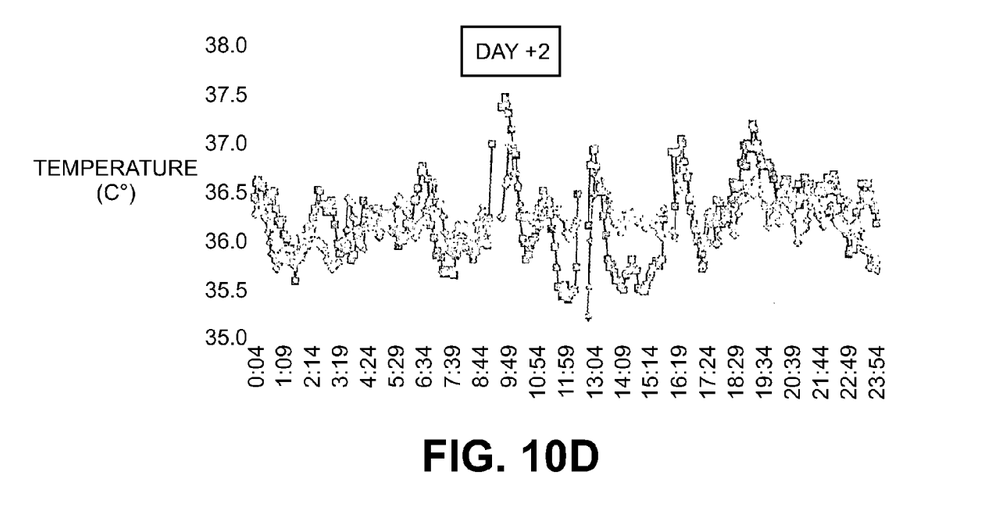
Figure 10E:
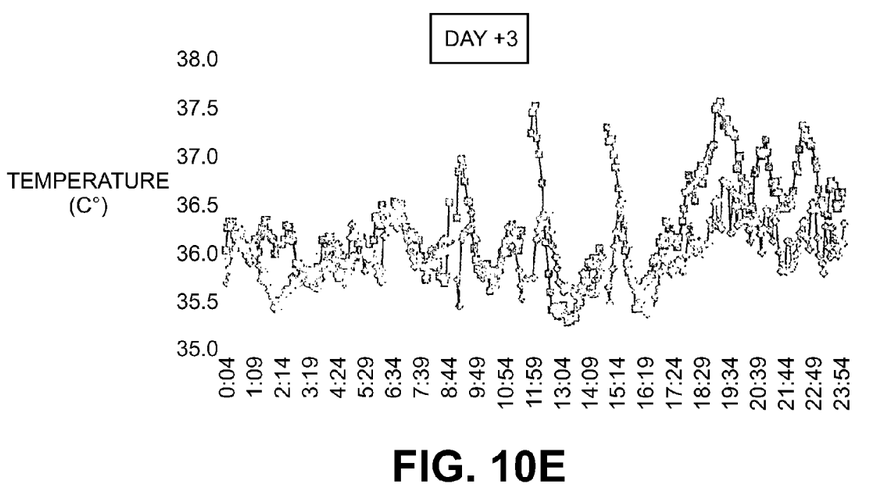
Figure 10F:
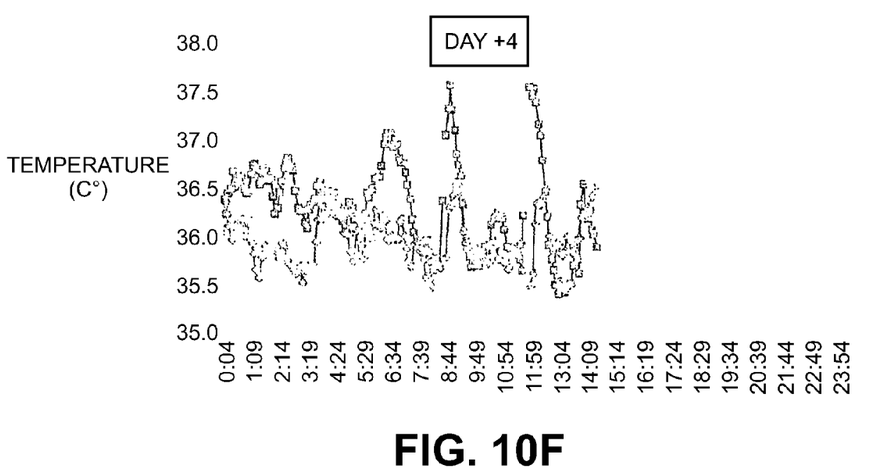

The aim of this experiment was to find out whether LG-acetylsalicylate acts as an NF-κB inhibitor in the mouse lung after H5N1 infection. For this purpose, it was investigated whether a treatment of the mice before and during the MB1 infection with LG-acetylsalicylate has an effect on the expression rate of the two chemokines or cytokines. For the experiment five Balb/c mice were each treated one hour before the infection (infection dose: 1×103 pfu/50 μl) i.v. (100 μl) and i.p. (200 μl) with 50 mM LG-acetylsalicylate. The further treatments were made 17, 24 and 42 hours after infection. After 48 hours p.i. the lungs were taken out and the RNA was isolated. The expression of IP10 and IFN-gamma in the mouse lungs of LG-acetylsalicylate-treated mice compared to the control animals was verified by means of quantitative RT-PCR. The data are shown in FIG. 9.

The expression of IP10 and IFN-gamma for untreated mice was set to 100%, in order to have a clearer possibility to compare. After four times treatment with LG-acetylsalicylate over the intravenous as well as intraperitoneal treatment route, a reduction of the m-RNA expression could be detected for both chemokines or cytokines. The intravenous treatment route showed with a 62% reduction for IP10 and a 68% reduction for IFN-gamma a stronger effect than for the intraperitoneal treatment route with 26% for IP10 and 50% for IFN-gamma.

The results show that the H5N1 virus-induced expression of NF-κB-dependent genes in LG-acetylsalicylate-treated infected mouse lungs is strongly reduced. This is important, since the excessive production of cytokines observed after H5N1 virus infection ("cytokine storm"), which cytokines in the largest part are regulated in an NF-κB-dependent manner, strongly contributes to the pathogenity of these viruses. Thus, LG-ASA cannot only directly influence the virus replication, but can also indirectly influence in a positive manner the course of the disease by reduction of excessive cytokine production.

Example 6

Compatibility Studies

In the following experiment, the compatibility of LG-acetylsalicylate after aerosol treatment of mice was tested. In order to monitor the influence of the treatment as precisely as possible, the experiment was carried out by means of the Mouse Monitoring System. This permits the measurement of the temperature in real time. Every 5 minutes a temperature value was determined and plotted (FIG. 10A-F). Further, the animals were weighed every day. At the end of the treatment, the mice were killed, and the organ weight of liver and spleen was determined. At the first signs of liver toxicity already, the size of the liver will increase. On the other hand, an increase of the size of the spleen is a sign of inflammation processes.

For the compatibility study, a Mouse Monitoring transmitter was implanted into in total 12 female Balb/c mice 3 days before the treatment. The successful intervention was monitored over 3 days. Then 6 mice were each treated three times per day with 2 ml of a 50 mM LG-acetylsalicylate solution by means of a Pari nebulizer. As controls served 6 mice, which were treated with 2 ml PBS. The solutions were nebulized with a pressure of 1.5 bar, so that the treatment took approx. 10 minutes. The treatment was carried out daily for 5 days at 9:00; 12:00 and 15:00 o'clock.

Figure 11:
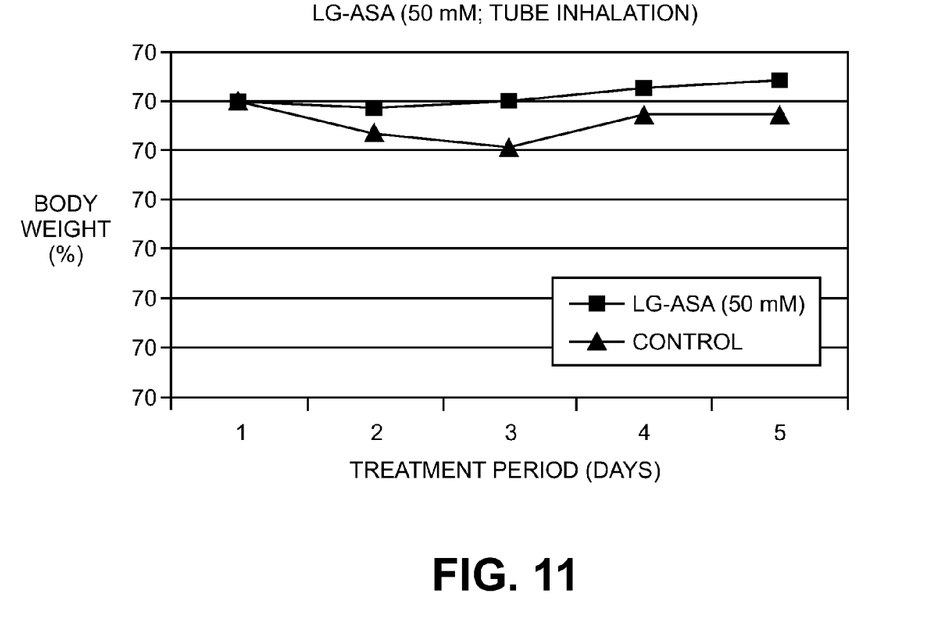
FIG. 11 shows that there is no significant difference of the changes of the body weight between the LG-acetylsalicylate group and the PBS-treated group.

The influence of LG-acetylsalicylate on the change of weight was investigated. All mice were weighed daily beginning with the day of treatment and that before the first treatment (9:00 o'clock). The weight of the first day of treatment was set to 100% and the determined body weight on the following days was referred thereto. The comparison of the two groups of treatment resulted in the plot shown in FIG. 11. There can be found that there is no significant difference of the changes of the body weight between the LG-acetylsalicylate group and the PBS-treated group.

Further, the influence of LG-acetylsalicylate on the body temperature was investigated.

As mentioned already, the Mouse Monitoring System permits the determination of the body temperature of mice in real time. Since mice have a high metabolism, smallest changes of well-being will already lead to changes of the body temperature. In FIG. 10, the course of the temperature beginning 1 day before the treatment (FIG. 10A) to the end of the treatment (day +4) (FIG. 10F) is shown. No difference with regard to the body temperature for LG-acetylsalicylate-treated mice compared to the control animals can be seen.

Figure 12A:
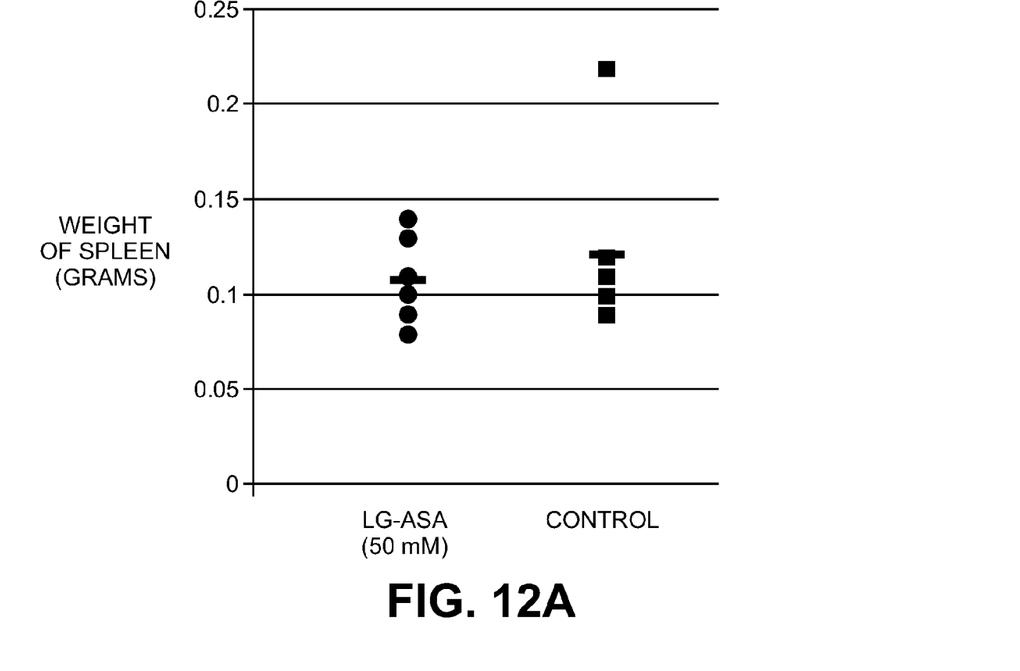
FIGS. 12A and 12B show influence of LG-acetylsalicylate on the weight of spleen (FIG. 12A) and liver (FIG. 12B).
Figure 12B:
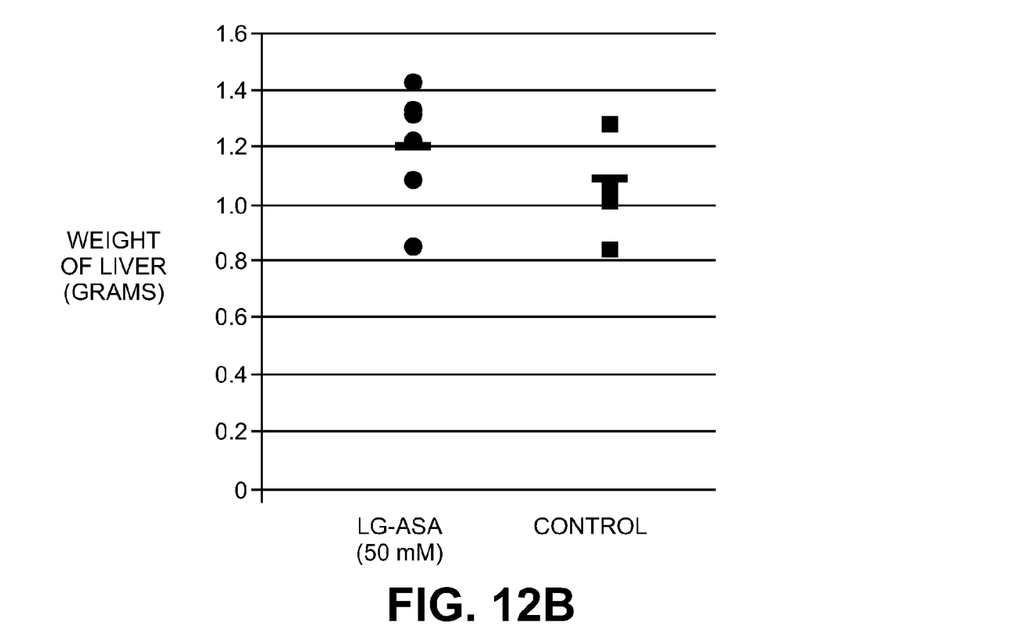

Finally, the influence of LG-acetylsalicylate on the weight of liver and spleen was investigated. Fifteen minutes after the last treatment, all animals were killed, and a necropsy was carried out. After complete exsanguination through the Vena Cava, the inner organs were examined. The lungs were first examined through the diaphragm in the not collapsing condition. Liver and spleen were weighed. The results are shown in FIG. 12. Since the body weight of the mice did not substantially change during the treatment, a normalization of the organ weights could be left out. For spleen (FIG. 12A) as well as for liver (FIG. 12B), no significant difference in the organ weights of LG-acetylsalicylate-treated animals and the control animals could be found. Thus, after inhalative treatment of mice, no signs for a liver toxicity, often accompanied with a swelling of the organ, are observed. Further, no systemic inflammation reactions, often accompanied with an increase of size of the spleen, were observed.

From the studies described above follows, as a summary, that the inhalative application of 2 ml LG-acetylsalicylate with a concentration of 50 mM over a time of 5 days is well compatible for mice.

Example 7

Patients Tests

In a healing attempt, 4 patients with bronchial infections were administered a solution, comprising up to 2M LG-ASA (50:50) and vaporized to particle sizes of less than 5 μm.

The total amounts of LG-ASA were up to 350 mg. The inhalation flow was adjusted to less than 500 ml/s, in most cases less than 300 ml/s. The breathing volume was at least 30%, in most cases at least 50%, of the inspiration capacity of the patients. For three of the patients, a significant improvement of the symptoms was detected already on the first day after the administration. For all other patients, an improvement of the symptoms occurred on the 3rd day after the administration. The subjectively perceived compatibility of these high concentrations in the solutions was excellent. No patient reported taste irritations. Further, no extra urge to cough was detected.

The invention claimed is:

1. A method for the treatment of an influenza A viral infection in a human or animal, wherein a pharmaceutical composition is administered to said human or animal, wherein said pharmaceutical composition comprises:

a salt of o-acetylsalicylic acid with a natural or non-natural basic amino acid; and a salt of o-acetylsalicylic acid with glycine, wherein the pharmaceutical composition is an aerosol formulation, and wherein said aerosol formulation is administered aerogenically through the nose or mouth to said human or animal in an amount effective to treat said influenza A viral infection.

2. The method of claim 1, wherein the basic amino acid is selected from the group consisting of lysine, arginine, omithine, diaminobutyric acid, and mixtures of such amino acids.

3. The method of use according to claim 2, wherein the basic amino acid is D-lysine, L-lysine or a mixture of D-lysine and L-lysine.

4. The method of claim 1, wherein the influenza A virus is of H5 or H7 type.

5. The method of claim 1, wherein the pharmaceutical composition is a galenic preparation comprising a liquid or aqueous composition.

6. The method of claim 5, wherein the pharmaceutical composition is an aqueous composition that is a 0.1 to 5 M, 0.1 to 3 M, or 1 to 3 M aqueous solution of said salt.

7. The method of claim 5, wherein the pharmaceutical composition is an aqueous composition that is a 0.01 to 100 mM or 0.1 to 10 mM aqueous solution of said salt.

8. The method of claim 1, wherein the composition is arranged in a pharmaceutically compatible tank with a vaporizer or nebulizer.

9. The method of claim 8, wherein the tank is prepared for the adjustment of an inhalation flow of less than 1,000 ml/s, less than 500 ml/s, or less than 300 ml/s, and of a breathing volume of at least 10-%, at least 30-%, at least 50-%, or up to 95-%, in reference to the inspiration capacity of a patient.

10. The method of claim 1, wherein at least 10 mg, at least 50 mg, at least 100 mg, or up to more than 200 mg, of the salt of o-acetylsalicylic acid is administered aerogenically.

11. The method of claim 1, wherein an inhalation flow of the aerogenically administered aerosol formulation is adjusted to less than 1,000 ml/s, less than 500 ml/s, or less than 300 ml/s is, and wherein a breathing volume of the aerogenically administered aerosol formulation is adjusted to at least 20-%, at least 30-%, at least 50-%, or up to 95-%, in reference to the inspiration capacity of a patient.

12. The method of claim 1, wherein the aerosol formulation is administered by means of an inhalation device with a supply tank and an aerosol generator connected to the supply tank.

13. The method of claim 12, wherein the inhalation device further comprises a control or regulation means for the control or regulation of the inhalation flow and of the breathing volume, wherein the control or regulation means are preferably adjusted to less than 1,000 ml/s, less than 500 ml/s, or less than 300 ml/s is, and wherein the breathing volume is adjusted to at least 20%, at least 30%, at least 50%, or up to 95%, in reference to the inspiration capacity of a patient.

14. The method of claim 1, wherein the salt of o-acetylsalicylic acid is a mono-acetylsalicylate.

15. The method of claim 1, wherein the aerosol formulation is administered aerogenically in less than 5 min, less than 2 min, or less than 1 min.

* * * * *